CHRYSANTHEMUM PLANT
Filed June 15, 1971 2 Sheets-Sheet 1
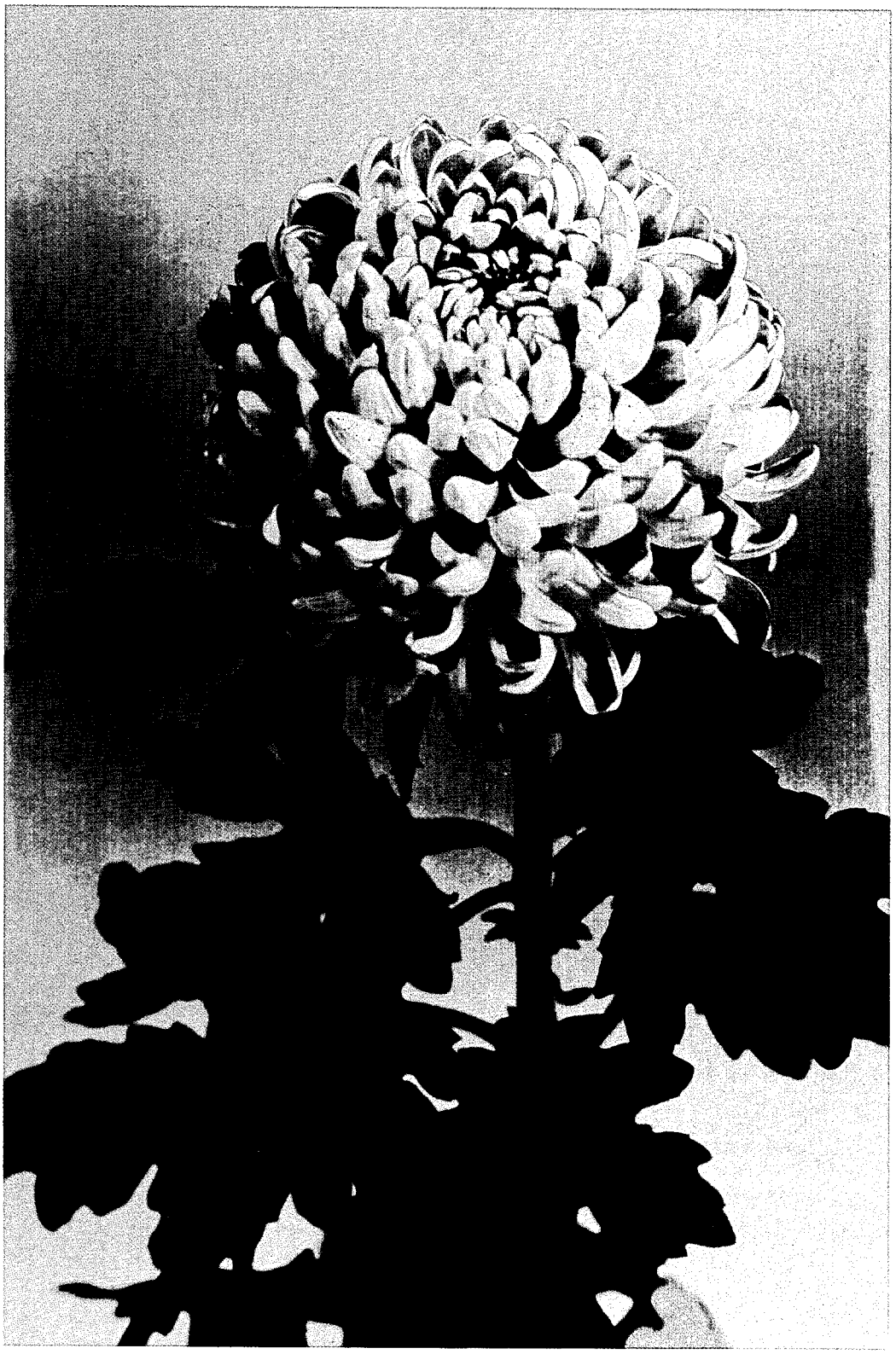

CHRYSANTHEMUM PLANT
Filed June 15, 1971 2 Sheets-Sheet 2
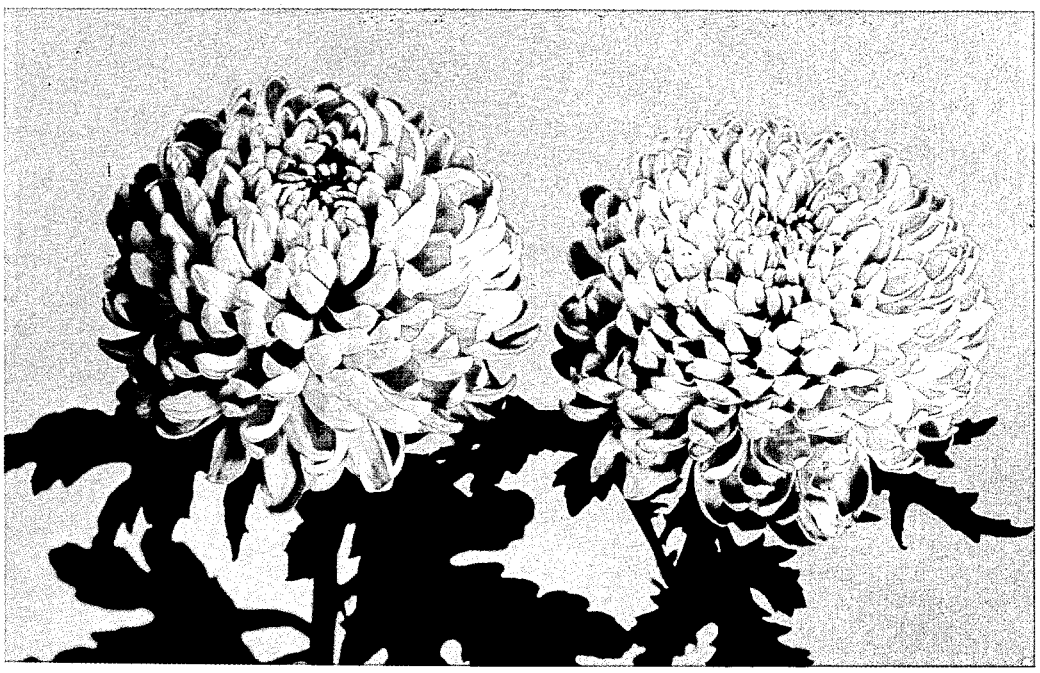
INVENTORS
WALTER H. JESSEL, Jr.,
WILLIAM E. DUFFETT
BY
Oberlin, Maky, Donnelly & Renner
ATTORNEYS

United States Patent Office

Plant Pat. 3,311

Patented Feb. 27, 1973

3,311
CHRYSANTHEMUM PLANT

Walter H. Jessel, Jr., Doylestown, and William E. Duffett, Akron, Ohio, assignors to Yoder Brothers, Inc., Barberton, Ohio

Filed June 15, 1971, Ser. No. 153,455

Int. Cl. A01h *5/00*

U.S. Cl. Plt.—80 1 Claim

The present invention comprises a new and distinct cultivar of chrysanthemum plant which is a sport of the unpatented but commercially well-known cultivar Escapade.

The new cultivar is similar in many respects to Escapade, having the same characteristics of:

(1) Similar foliage shape.

(2) A heavy stem.

(3) Resistance to sun scald.

The new variety is distinguished from Escapade by the following characteristics:

(1) Approximately ½" to 1¼" larger flowers, depending on temperature.

(2) Lower petals less incurved, more loose in form.

(3) 6 to 9 days later response.

(4) 6"–10" more vigor, depending on culture.

(5) The color on the reverse side of the petals is somewhat lighter.

Calif.; Fort Myers, Fla.; and Barberton, Ohio, responds as a late 9 week variety. The response time, color and blooming period may vary significantly with varying environmental conditions such as temperature, day length, and light intensity. Suggested flowering in the northern and western United States is from June through mid-November; in the southern states, year round; in coastal California it is not recommended due to the cooler environment, which produces a longitudinal petal roll. It is also not recommended in Florida under outdoor culture.

The accompanying drawings show the color and form of the new cultivar, with the colors being as nearly true as possible with color illustrations of this type. Sheet 1 shows the new cultivar by itself, and sheet 2 is a comparison view showing the new cultivar on the left and the parent cultivar Escapade on the right. Although, as above indicated, the flower size of the new cultivar is larger than the flower size of Escapade, such size difference is not completely discernible from the comparison photo.

In the description which follows, based on observations made of the new cultivar in a greenhouse in Barberton, Ohio, color references are to the Munsell Color Book, 1963 edition; and comparisons have been made with the parent cultivar Escapade. Where only a single value or description appears for the new cultivar, the same value or description applies also to the comparison cultivar.

Botanical Classification: *Chrysanthemum morifolium*

| | Serenade | Escapade |
|---|---|---|
| Bloom: | | |
| Size | 5½" to 6¼" in diameter; under coastal California and Florida conditions size is 3"–6½". | 5". |
| Fully expanded | 6½"–7" | 5¾". |
| Borne | Singly on disbudded plant | |
| Stems | Heavy and strong | |
| Form | Semi-incurved | |
| Permanence | 7–10 days | |
| Color: | | |
| Center of flower | Lavender, 5RP7/4 | Lavender, 5RP6/6. |
| Base of petals | Grey-lavender, 5RP8/2 | Grey-lavender, 5RP8/2. |
| Inside of petals | Lavender pink, 10P7/6 | Lavender pink, 10P7/6. |
| Reverse of petals | Pale lavender, 10P8/4 | Pale lavender, 10P8/2. |
| Tonality from a distance. | Lavender | Lavender pink. |
| Discoloration | Light lavender, 5RP6/6 | Light lavender, 10P8/2. |
| Petals: | | |
| Texture | Smooth | |
| Appearance | Very broad slightly open at base, wide toward extremity tapers sharply | |
| Arrangement | Composite, whorled on a single receptacle | |
| Persistence | Resists shatter | |
| Fragrance | Typical chrysanthemum | |
| Reproductive organs: | | |
| Stamen, anthers | None | |
| Pollen | None | |
| Arrangement | Clustered in center of flower, if present | |
| Styles | Present in both ray and disc florets | |
| Length | Short | |
| Ovaries | At base of petals attached to receptacle | |
| Plant: | | |
| Form | Herbaceous | |
| Growth | Upright | |
| Height, depending on culture. | Approximately 44"–48" grown as a single stem crop given 3–4 long day weeks and 13–14 weeks total crop time for the various seasons of the seasons of the year as defined in the timetables published by Yoder Brothers, Inc. | Approximately 37"–38" grown as a single stem crop given 3–4 long day weeks and 13–14 weeks total crop time for the various seasons of the year as defined in the timetables published by Yolder Brothers, Inc. |
| Spread | None; little if grown pinched | |
| Foliage: | | |
| Top side | Dark green, 10GY2/4 | |
| Size | 8"–8½" long, 5½" wide | 7"–8½" long, 5" wide. |
| Quantity | Numerous | |
| Shape | Palmate | |
| Texture | Smooth | |
| Ribs and veins | Prominent | |
| Edge | Indented | |
| Serration | Very slight | Slight. |
| Underside | Light green, 7.5GY5/4 | |
| Stipules | Present | |

(6) Foliage larger than parent.

(7) The overall appearance of the flower is more generally lavender as compared with the pink lavender appearance of Escapade.

The new cultivar was discovered upon examination of a flowering block of the parent variety at Barberton, Ohio, and when asexually reproduced by cuttings at Barberton, Ohio, has been found to retain its distinctive characteristics through successive propagations.

The new cultivar when grown in the vicinity of Salinas,

We claim:

1. A new and distinct cultivar of chrysanthemum characterized particularly as to uniqueness when compared to the parent cultivar Escapade by its looser, less incured petal form; larger flower size; 6–9 days later response and 6–10 inch additional vigor; larger foliage; and its more generally lavender overall flower color.

No references cited.

ROBERT E. BAGWILL, Primary Examiner